United States Patent
Oh (10) Patent No.: US 12,298,268 B2
(45) Date of Patent: May 13, 2025

(54) SINGLE-USE DISPOSABLE REFERENCE SENSOR

(71) Applicant: Nova Biomedical Corporation, Waltham, MA (US)

(72) Inventor: Bong Kyun Oh, Newtonville, MA (US)

(73) Assignee: Nova Biomedical Corporation, Waltham, MA (US)

( * ) Notice: Subject to any disclaimer, the term of this patent is extended or adjusted under 35 U.S.C. 154(b) by 149 days.

(21) Appl. No.: 16/879,877

(22) Filed: May 21, 2020

(65) Prior Publication Data

US 2021/0364463 A1 Nov. 25, 2021

(51) Int. Cl.
*G01N 27/30* (2006.01)
*G01N 27/40* (2006.01)
*G01N 27/401* (2006.01)

(52) U.S. Cl.
CPC ......... *G01N 27/301* (2013.01); *G01N 27/307* (2013.01); *G01N 27/40* (2013.01); *G01N 27/401* (2013.01)

(58) Field of Classification Search
CPC .... G01N 27/301; G01N 27/307; G01N 27/40; G01N 27/401
See application file for complete search history.

(56) References Cited

U.S. PATENT DOCUMENTS

| | | | |
|---|---|---|---|
| 4,053,382 A | 10/1977 | Maruyama et al. | |
| 4,615,983 A * | 10/1986 | Koyama | G01N 33/525 436/514 |
| 4,653,499 A * | 3/1987 | Murray, Jr. | G01N 27/3335 600/348 |
| 4,734,184 A * | 3/1988 | Burleigh | G01N 33/492 204/411 |
| 4,816,131 A * | 3/1989 | Bomsztyk | G01N 33/492 204/403.13 |
| 4,871,439 A * | 10/1989 | Enzer | G01N 27/4165 204/411 |
| 4,933,048 A | 6/1990 | Lauks | |
| 5,346,606 A | 9/1994 | Christner et al. | |
| 6,551,480 B1 | 4/2003 | Taagaard et al. | |

(Continued)

FOREIGN PATENT DOCUMENTS

DE 3100302 A1 12/1981
EP 0639767 A3 2/1995

(Continued)

OTHER PUBLICATIONS

JPH08225626, machine translation (Year: 1996).*
International Search Report received in International PCT Application No. PCT/US2021/019524, dated May 26, 2021, 10 pages.

*Primary Examiner* — C. Sun
(74) *Attorney, Agent, or Firm* — Hayes Soloway PC (57) ABSTRACT

A single-use disposable potentiometric reference sensor includes an insulating base substrate, a reference electrode disposed on the insulating base substrate where the reference electrode is a silver-silver chloride electrode, an internal layer disposed on the reference electrode where the internal layer is an amorphous salt layer that includes an amorphous polysaccharide and a salt having equi-mobility cations and anions, and a semipermeable cover membrane disposed over the internal layer where the semipermeable cover membrane has water vapor and ion permeability.

18 Claims, 6 Drawing Sheets

(56) References Cited

U.S. PATENT DOCUMENTS

| | | | |
|---|---|---|---|
| 6,579,440 B2 | 6/2003 | Connelly et al. | |
| 7,767,068 B2 | 8/2010 | Lauks et al. | |
| 2001/0024804 A1 | 9/2001 | Shen | |
| 2002/0003087 A1* | 1/2002 | Chih-hui | G01N 27/3272 204/400 |
| 2004/0231984 A1* | 11/2004 | Lauks | G01N 27/301 204/431 |
| 2006/0137980 A1 | 6/2006 | Lauks et al. | |
| 2008/0011607 A1 | 1/2008 | Iwamoto et al. | |
| 2008/0149482 A1* | 6/2008 | Marett | G01N 27/301 204/414 |
| 2011/0220497 A1 | 9/2011 | Wells et al. | |
| 2018/0067110 A1* | 3/2018 | Van Lieshout | G01N 33/54366 |
| 2018/0328877 A1* | 11/2018 | Vaddiraju | C23C 14/205 |
| 2019/0117823 A1* | 4/2019 | Jollez | B01J 20/321 |
| 2019/0195824 A1 | 6/2019 | Speck | |
| 2020/0318152 A1* | 10/2020 | Xu | B01D 69/144 |

FOREIGN PATENT DOCUMENTS

| | | |
|---|---|---|
| EP | 1644726 A1 | 4/2006 |
| EP | 2293054 A1 | 3/2011 |
| KR | 20080050951 A | 6/2008 |
| WO | 2005008232 A1 | 1/2005 |
| WO | 2006085761 A1 | 8/2006 |
| WO | 2012074356 A1 | 6/2012 |
| WO | 2021236189 A1 | 11/2021 |

* cited by examiner

SINGLE-USE DISPOSABLE REFERENCE SENSOR

BACKGROUND OF THE INVENTION

1. Field of the Invention

The present invention relates generally to electrochemical sensors. Particularly, the present invention relates to electrochemical potentiometric reference sensors. More particularly, the present invention relates to planar electrochemical potentiometric reference sensor with membrane coatings.

2. Description of the Prior Art

The basic prior-art electrochemical sensor typically consists of an electrochemical cell with two electrodes. The first electrode is responsive to a chemical species in a liquid sample and is generally called the indicator electrode. The second electrode is a reference electrode that is non-responsive to changes in the composition of the liquid sample and provides a constant potential with respect to which is measured the potential developed by the indicator electrode from the liquid sample.

In the past, chemistry analyzers for the quantitative measurement of chemical species in liquid samples including blood typically included a very complex fluidic structure for washing and calibrating of multiple-use sensors. Thus, manufacturers of such chemistry analyzers have attempted to produce sensors at relatively low cost, so they are used as single-use devices. A technology suitable for such sensor devices is planar technology. Sensors made by planar technology have included both thick-film and thin-film technologies.

The typical components of construction of a planar electrochemical sensor of the prior art is a device that includes a plurality of metal conductor elements on a planar insulating substrate. The planar electrochemical sensor of the prior art consists of multiple layers over the plurality of metal conductor elements where one end of the plurality of metal conductor elements is exposed for connection to an external measuring circuit while a second end of the plurality of metal conductor elements is exposed for receiving multiple coatings forming an integral electrolyte layer that includes a hydrophilic layer such as a gel material to act as an aqueous electrolyte as well as other reagents selected for measuring specific species in the liquid sample. The chemical species from the liquid sample undergo an electrochemical reaction at the electrode surface generating a current or voltage. The generated current or voltage is typically proportional to the concentration of the chemical species in the liquid sample provided, however, that the reference electrode remains stable throughout the measurement process.

In order to provide an electrode that is useful in numerous processes such as, for example, for blood analysis operations in hospitals, blood chemistry labs and the like, it is desirable to provide an electrode that is small, has a long shelf life and is inexpensive to be economically disposable. Most prior art electrodes employ hydrophilic or aqueous reference electrolytes making long shelf life difficult to achieve. Hydrophilic electrolytes are hydrated gels or the like to allow ion transport. Shipping and storing "wet" electrolytes involve relative complex packaging.

A salt bridge potentiometric reference electrode consists of a silver/silver chloride (Ag/AgCl) base electrode, which is in contact with concentrated aqueous salt solution, preferably an equi-mobility salt such as potassium chloride. Concentrated chloride ions saturate Ag/AgCl potential while equi-mobility potassium and chloride prevent junction potential development at the reference sensor and sample interface. To hold the stable reference potential for a prolonged period, the amount of salt in the array reservoir is critical. In a planar sensor array, the size of the salt reservoir is very limited and it can be washed away quickly (i.e. less than a second) once it comes into contact with aqueous solution. There have been many efforts to solve this issue by trying various cover membranes, which have not been very successful. Previous attempts failed mainly due to the hydrophobic cover membrane polymer's poor water vapor diffusion property and too slow (or too fast) salt permeability across the membrane.

Currently a few different single use potentiometric reference sensor technologies have been reported. U.S. Pat. No. 4,933,048 (Lauks, 1990) discloses an open junction reference electrode assembly. The reference electrode assembly includes a metallic member that is coated with an electrode material reversible to an ion X and a layer of an electrolyte containing ion X formed over the electrode. The electrolyte extends beyond the perimeter of the electrode. The portion of the electrolyte extending beyond the perimeter of the electrode is overlaid by a membrane which is permeable to $H_2O$ molecules but not permeable to ion X. A portion of the electrolyte extends through the permeable membrane or is otherwise enabled to form a liquid junction with the sample solution at a position relatively distant from the electrode. Accordingly, the ions must diffuse along a relatively long path through the electrolyte between the liquid junction and the electrode providing a long time constant for ion diffusion while the electrolyte may be "wet-up" relatively quickly. As a result, there is a period of time after the electrolyte to wet-up and before ion diffusion affects ionic concentrations in the vicinity of the electrode during which the potential of the electrode is substantially constant. The electrolyte is composed of concentrated salt containing hydrophilic polymer film as an inner layer and is partially covered with hydrophobic membrane that can expose a small part of the inner layer directly to a sample solution. To achieve this type of configuration, the process of sensor manufacturing is complicated, which can lead to an increase in sensor failure rates.

U.S. Pat. No. 7,767,068 (Lauks et al., 2010) discloses heterogeneous membrane electrodes. The heterogeneous membrane consists of a mixture of oil and water-soluble compartments. The aqueous part is made up of salts and redox couples containing a cross-linkable hydrophilic polymer. The oil part is composed of a cross-linkable hydrophobic polymer. This mixture emulsifies in order to support a manufacturing process using either dispensing or printing. The next steps require settling of the deposited layer, degassing and finally UV curing to immobilize all the compartments. This procedure is a complicated time reliant process due to the phase separation characteristics of the heterogeneous membrane which could induce sensor to sensor variations.

SUMMARY OF THE INVENTION

It is well known that a potentiometric reference electrode must be dependable by providing a stable potential and not prone to environmental factors. All potentiometric reference electrodes have liquid junction potentials. These are the boundary/interface potentials that develop between the reference electrode and the sample. Notwithstanding that all potentiometric reference electrodes have junction potentials, it is imperative that the junction potential is relatively constant and unaffected by temperature or local chemical composition around the reference electrode.

Integrating an electrochemical potentiometric reference electrode within a planar sensor array is the key challenge in a single-use planar sensor.

It is important that any single-use, potentiometric reference electrode incorporated into a planar sensor array have a relatively constant and reproducible junction potential where the concentration of various electrolytes in a blood sample likely vary depending on the health of the animal from which the blood sample is taken. As previously discussed, planar sensor arrays have potentiometric reference electrodes with very limited size of the salt reservoir. In order to prevent the limited size of the salt reservoir from washing away quickly when exposed to a blood sample, a hydrophobic component must be incorporated in the potentiometric reference electrode to prevent this from happening or to delay for a period of time any change in the reference potential or the reference electrode's junction potential during which a measurement of the blood sample is being made.

It is an object of the present invention to provide a disposable, single-use electrochemical potentiometric reference electrode/sensor. It is another object of the present invention to provide a disposable, single-use, potentiometric reference electrode/sensor that has a relatively long shelf life. It is a further object of the present invention to provide a salt-bridge, electrochemical potentiometric reference electrode/sensor having dry reagents that reach an active state after water-vapor absorption at the point of use.

The present invention achieves these and other objectives by providing a single-use disposable potentiometric reference sensor that includes combining an amorphous polysaccharide/salt layer with a semipermeable cover membrane.

In one embodiment, the single-use disposable potentiometric reference sensor includes an insulating base substrate, a reference electrode disposed on the insulating base substrate where the reference electrode is a silver-silver chloride electrode, an internal layer disposed on the reference electrode where the internal layer is an amorphous salt layer that includes an amorphous polysaccharide and a salt having equi-mobility cations and anions, and a semipermeable cover membrane disposed over the internal layer where the semipermeable cover membrane has water vapor and ion permeability.

In one embodiment, the amorphous polysaccharide has amorphous properties such that when over saturated with the salt, the amorphous polysaccharide and salt do not separate when the internal layer is formed.

In one embodiment, the amorphous polysaccharide is selected from various compounds including, but not limited to, pullulan, dextran and amylose.

In one embodiment, the salt is one of potassium chloride, ammonium chloride, potassium nitrate, lithium acetate, and the like where the cations and anions have substantially equi-mobility.

In one embodiment, the semipermeable cover membrane is a made of chlorosulfonated polyethylene or made of cellulose acetate butyrate polymers.

In another embodiment, the single-use disposable electrochemical sensor includes an insulating base substrate having a sensing surface, a potentiometric working electrode formed on the sensing surface where the potentiometric working electrode has a species-specific reagent matrix disposed thereon where the species-specific reagent matrix has one or more layers selected for measuring a specific species in a liquid sample, and a potentiometric reference electrode formed on the sensing surface where the reference electrode is a silver-silver chloride electrode having a multi-layer reference coating thereon. The multi-layer reference coating has an internal layer disposed on the Ag/AgCl reference electrode where the internal layer includes an amorphous polysaccharide and a salt having equi-mobility cations and anions, and a semipermeable cover membrane disposed over the internal layer, the semipermeable cover membrane being a semipermeable hydrophobic polymer where the semipermeable cover membrane has water vapor permeability and ion permeability.

In one embodiment, a method of forming a single-use disposable potentiometric reference sensor includes providing a sensor body having an insulating base substrate with at least one conductive path and an insulating and reagent holding layer disposed onto the insulating base substrate where the insulating and reagent holding layer over the insulating base substrate has at least one reagent holding opening where the at least one reagent holding opening exposes a portion of the at least one conductive path, disposing an amorphous salt layer mixture containing an amorphous polysaccharide and a salt having equi-mobility cations and anions into one of the at least one reagent holding opening, drying the amorphous salt layer mixture forming an internal layer, disposing a cover membrane solution containing a hydrophobic polymer over the internal, hydrophilic layer, and drying the cover membrane solution forming a semipermeable cover membrane where the semipermeable cover membrane has water vapor permeability and ion permeability.

In one embodiment, the amorphous salt layer mixture is formed by adding together a plurality of components comprising a predefined amount of the amorphous polysaccharide and a predefined amount of 3 mol/L salt solution, and mixing the plurality of components forming the amorphous salt layer mixture.

In one embodiment, the amorphous salt layer mixture is formed by measuring 750 milligrams of the amorphous polysaccharide, measuring a volume of 3 milliliter of the 3 mol/L salt solution, and mixing the plurality of components forming the amorphous salt layer mixture.

In one embodiment, the cover membrane solution is formed by measuring a predefined amount of the hydrophobic polymer that is one of chlorosulfonated polyethylene or cellulose acetate butyrate and mixing the hydrophobic polymer in a predefined amount of THF/cyclohexanone forming the cover membrane solution.

In one embodiment, the cover membrane solution is formed by measuring 8-10 wt % of one of the chlorosulfonated polyethylene or the cellulose acetate butyrate and mixing the hydrophobic polymer in a predefined amount of THF/cyclohexanone forming the cover membrane solution.

In a further embodiment, a method of forming a single-use, disposable, electrochemical potentiometric reference sensor includes providing a sensor body having an insulating base substrate with at least one conductive path, and an insulating and reagent holding layer disposed onto the insulating base substrate where the insulating and reagent holding layer has at least one reagent holding opening where the at least one reagent holding opening exposes a portion of the at least one conductive path, disposing an amorphous salt layer mixture containing an amorphous polysaccharide and a salt having equi-mobility cations and anions into one of the at least one reagent holding opening, drying the amorphous salt layer mixture forming an internal layer, disposing a cover membrane solution containing a hydrophobic polymer over the hydrophilic internal layer, and drying the cover membrane solution forming a semipermeable cover membrane where the semipermeable cover membrane has water vapor permeability and ion permeability.

In one embodiment, a multi-layer reagent matrix for making a potentiometric reference electrode into a single-use, disposable reference sensor is disclosed. The multi-layer matrix includes an internal layer formed from an amorphous salt layer mixture containing an amorphous polysaccharide and a salt where the internal layer overlays the Ag/AgCl reference electrode. The amorphous polysaccharide has amorphous properties such that when over saturated with the salt, the amorphous polysaccharide and the salt do not separate when the internal layer is formed. A hydrophobic cover membrane formed from a cover membrane solution is disposed over the internal layer, the cover membrane solution containing a hydrophobic polymer where the hydrophobic semipermeable membrane polymer is water vapor and ion permeable.

In one embodiment, the internal layer is a mixture of potassium chloride and at least one of pullulan, dextran and amylose.

DETAILED DESCRIPTION OF THE INVENTION

The present invention is illustrated in FIGS. 1-8. In one embodiment, a disposable, single-use potentiometric reference sensor 10 of the present invention is one portion of a disposable, single-use electrochemical sensor 5 made using a 2-layer construction (See FIGS. 1-4). The 2-layer construction has a laminated body 12 that includes an electrode end portion 14, an electrical contact end portion 16, a working electrode 17, a reference electrode 18 at electrode end portion 14, and electrical contact pads 16a and 16b at electrical contact end portion 16. Laminated body 12 also includes an electrically insulating base layer 20, and an electrically insulating and electrode delineating layer 30. All layers of laminated body 12 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene, polystyrene, and the like.

Insulating base layer 20 has an electrically conductive layer 21 on which is delineated at least two electrically conductive paths 22 and 24. The electrically conductive paths 22 and 24 may be formed by scribing or scoring electrically conductive layer 21, or by silk-screening electrically conductive paths 22 and 24 onto insulating base layer 20. Scribing or scoring of conductive layer 21 may be done by mechanically scribing the electrically conductive layer 21 creating a non-electrically conductive scoring line 28 sufficiently to create the at least two independent conductive paths 22 and 24. The preferred scribing or scoring method of the present invention is done by using a carbon dioxide laser, a YAG laser or an excimer laser. Conductive layer 21 may be made of any electrically conductive material such as, for example, copper, gold, tin oxide/gold, palladium, other noble metals or their oxides, or carbon film compositions. The electrically conductive material used in this embodiment is palladium. An acceptable thickness for base layer 20 is in the range of 0.002 in (0.05 mm) to 0.010 in (0.25 mm). One such usable material for base layer 20 is a 0.005 in (0.125 mm) palladium polyester film (Stock. No. Melinex 329) sold by Marian, Inc., Indianapolis, Indiana The insulating and electrode delineating layer 30 has at least two openings 32 and 34. Opening 32 exposes a portion of conductive path 22, and opening 34 exposes a portion of conductive path 24 creating reagent holding wells. In this embodiment, insulating and electrode delineating layer 30 is a medical grade one-sided adhesive tape/film available from Transcendia, Inc., Franklin Park, Illinois Acceptable thicknesses of the tape for use in the present invention are in the range of about 0.001 in. (0.025 mm) to about 0.005 in. (0.13 mm). One such tape/film, Stock No. PE31280 (about 0.002 in. (0.045 mm)), is used due to its ease of handling and good performance in terms of its ability to hold a sufficient quantity of chemical reagents. It should be understood that the use of a tape is not required. Insulating and electrode delineating layer 30 may be made from a plastic sheet and may be coated with a pressure sensitive adhesive, a photopolymer, ultrasonically-bonded to base layer 20, silk-screened onto base layer 20, or 3-D printed onto base layer 20 to achieve the same results as using the polyester tape mentioned.

The at least two openings 32 and 34 define electrode areas W and R, respectively, forming a working electrode W, and a reference electrode R. Generally, working electrode W is loaded with a reagent matrix deposited directly onto a portion of the conductive layer 21 exposed in electrode area W where the reagent matrix is formulated for measuring a specific species in the liquid sample. It is contemplated that second, third and more working electrodes may be incorporated in the electrochemical sensor in combination with the one reference sensor 10. It is also contemplated that the reference sensor may be a separate, independent sensor from any one of the one or more working electrodes for measuring a sample liquid and still function properly provided that the working electrodes and the reference sensor 10 contact the same liquid sample.

In the combination sensor, the working electrode and the reference electrode are each in electric contact with separate conductive paths 22 and 24, respectively. The separate conductive paths terminate and are exposed for making an electric connection to a reading device on the end opposite the electrode end portion 14 of laminated body 12.

The size of the reagent holding openings is preferably made as small as possible while still being capable of holding sufficient chemical reagent for the sensor(s) to function properly. The shape of the reagent holding openings in this embodiment is round and has a diameter of about 0.03 in. (about 0.76 mm). The two reagent holding openings 32, 34 are aligned with each other and are spaced about 0.0256 in. (0.65 mm) from each other. The circular reagent holding openings are for illustrative purposes only. It should be understood that the shape of the reagent holding openings is not critical and that the size of the openings is driven more by the technical feasibility of dispensing the reagent matrix mixture into the openings and other manufacturing limitations.

The possible electrode arrangements when the reference sensor is coupled with a flow cell should be W-R. If two or more working electrode sensors are included, then the arrangement should be W-W-R with the arrangement listed as the arrangement of electrodes would appear based on the sample flow direction across the working electrode sensor W first, and then across the reference electrode sensor R last. In other words, the fluid sample enters the flow cell 70, the fluid sample would cover the working electrode sensor W first and then the reference electrode sensor R. The positional arrangement is important in this case because the releasing of KCl ions from the reference sensor may contaminate the working electrode sensors if the working electrode sensors are downstream from the reference sensor.

Preferably, the potentiometric reference electrode 18 (electrode well 34) may be loaded with a Ag/AgCl layer (e.g., by applying Ag/AgCl ink or by sputter-coating (a) a Ag layer followed by chloridizing the Ag or (b) a Ag/AgCl layer) or other reference electrode materials that do not require a redox mediator to function properly. Disposed/deposited on the Ag/AgCl layer is a hydrophilic internal layer. The internal layer is an amorphous structure layer that is an amorphous salt layer. The amorphous salt layer includes an amorphous polysaccharide and a salt having equi-mobility cations and anions.

Figure 3:
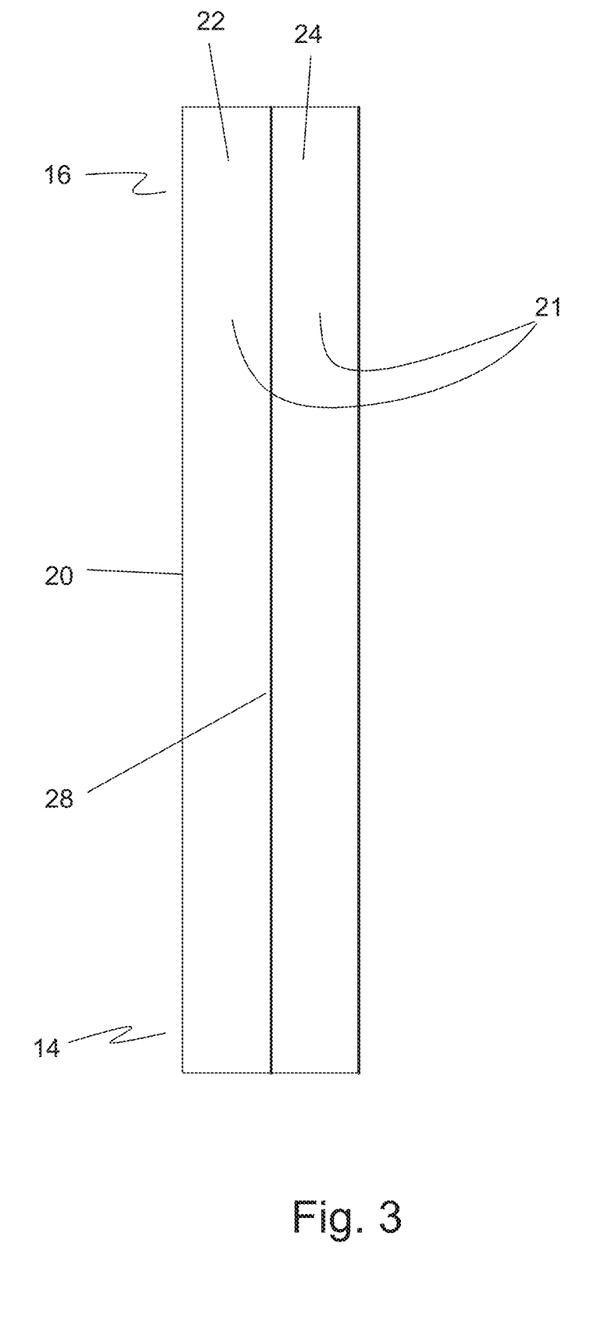
FIG. 3 is a top view of the electrically-insulating base layer of the potentiometric reference sensor.
Figure 4:
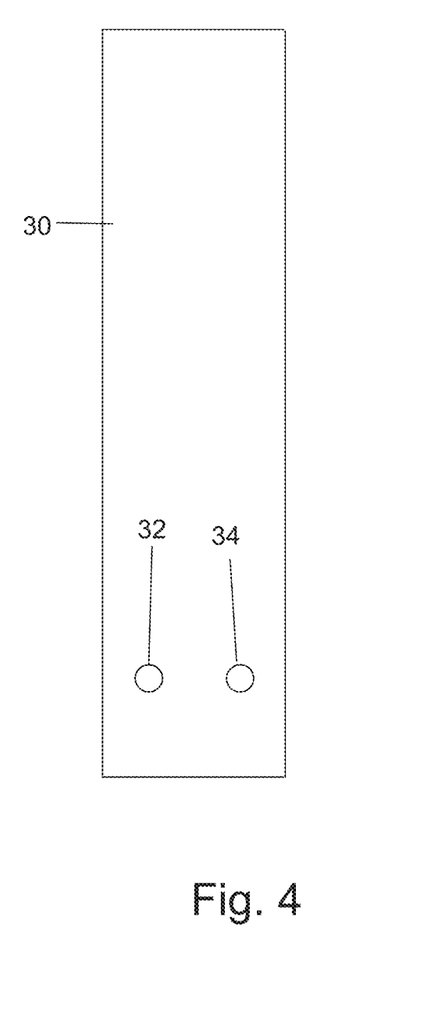
FIG. 4 is a top view of the electrically-insulating reagent holding layer.

Turning now to FIGS. 3 and 4, there is illustrated top views of base layer 20 and insulating and reagent holding layer 30. As illustrated in FIG. 3, the symmetry of the conductive paths is such that either longitudinal end of base layer 20 may be designated as either electrode end portion 14 or electrical contact end portion 16 depending on the orientation of the insulating and reagent holding layer 30 relative to base layer 20 and the assembly process. In this embodiment, base layer 20 has scribe marks in the conductive layer 21 delineating two separate conductive paths. It should be understood that the insulating base layer may have one, two, or more conductive paths where the additional conductive paths may be designated for similar or other analyte sensor reagents making the electrochemical sensor a multi-analyte sensor.

FIG. 4 is a top view of insulating and reagent holding layer 30. Insulating and reagent holding layer 30 has two or more openings that are spaced from each other such that each opening coincides with one of the conductive paths delineated on base layer 20. It is clearly understood that, if only the reference electrode is being made, the insulating and reagent holding layer would include only one conductive path on base layer 20. It should be understood that the electrically conductive path(s) disclosed herein may be made from any non-corroding metal. Carbon deposits such as for example carbon paste or carbon ink may also be used as the electrically conductive paths, all as is well known by those of ordinary skill in the art.

Figure 1:
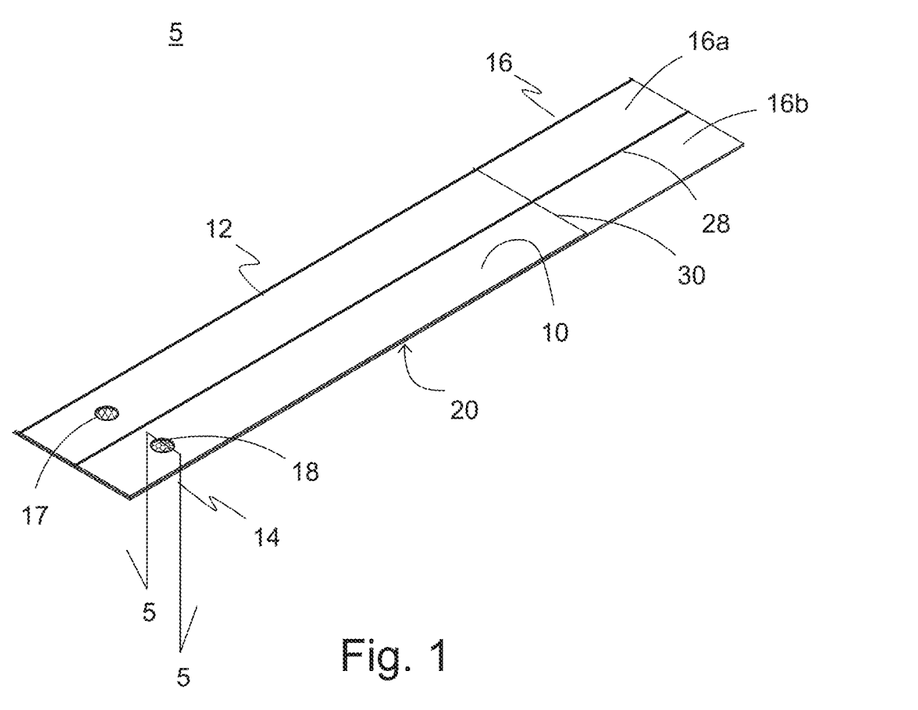
FIG. 1 is a perspective view of one embodiment of the present invention showing the potentiometric reference sensor.
Figure 5:
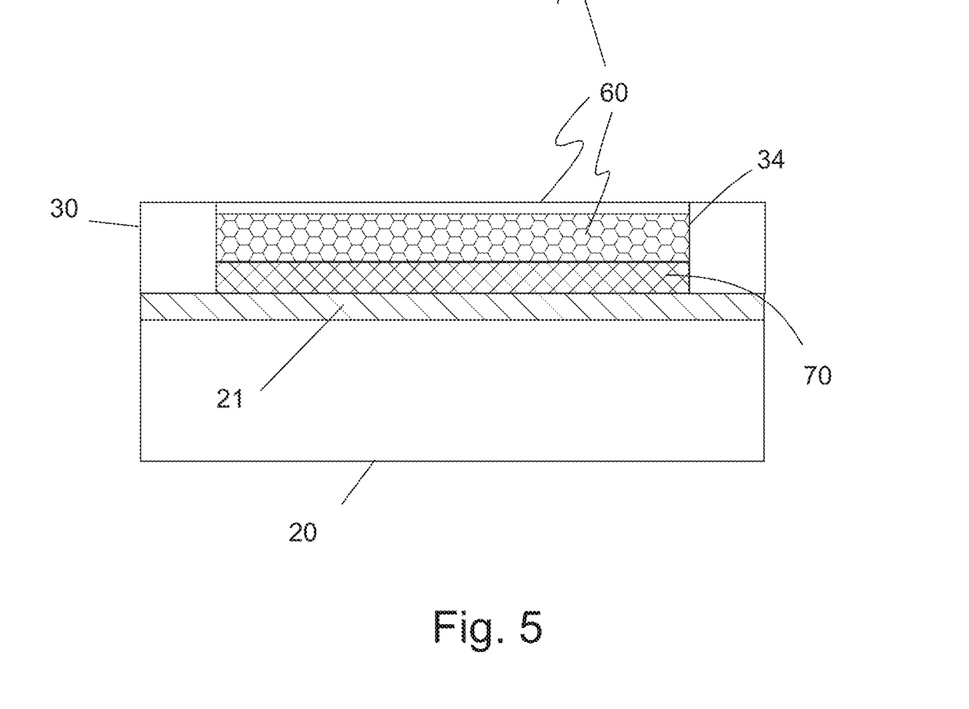
FIG. 5 is an enlarged, cross-sectional view of the potentiometric reference sensor taken along line 5-5 in FIG. 1.

Turning now to FIG. 5, there is illustrated an enlarged, cross-sectional view of the reference sensor 10 taken along line 5-5 in FIG. 1. It should be understood that the relative sizes of the layers 20, 30, metal coating 21, the electrode well 34, and the potentiometric reference electrode reagent matrix 60 are not to size but merely to illustrate the various components of reference sensor 10. As seen in FIG. 5, insulating base layer 20 has electrically conductive layer 21 disposed thereon and the Ag/AgCl layer 70 formed onto conductive layer 21. Insulating and reagent holding layer 30 has reagent holding opening 34 containing the potentiometric reference electrode reagent matrix 60.

Figure 6:
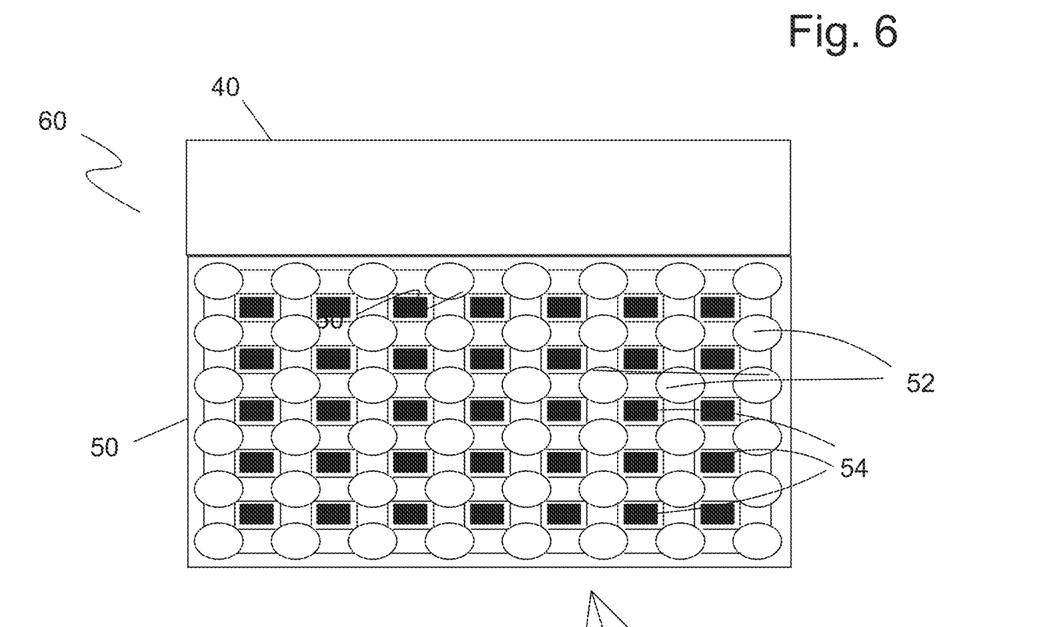
FIG. 6 is an enlarged view of the multi-layer reagent matrix of the potentiometric reference electrode showing the internal layer and the hydrophobic cover membrane layer.

FIG. 6 is an enlarged view of potentiometric reference electrode reagent matrix 60. Multi-layer reagent matrix 60 includes a hydrophilic polymer layer 50 and a hydrophobic polymer layer 40. Internal layer 50 includes an amorphous polysaccharide 52 and a salt 54. Hydrophobic cover membrane layer 40, as the name implies, is not water soluble but is water vapor and ion permeable.

The polymer used as the internal layer 50 should be sufficiently water-soluble and should also be capable of stabilizing all other chemicals in the reagent to the conductive surface layer 21 in the electrode area. Suitable polymers include, but are not limited to, amorphous polysaccharides, including but not limited to, pullulan, dextran, amylose, and the like. The internal layer 50 may be a single polymer or a combination of polymers preferable in a concentration range of about 0.02% (w/w) to about 7.0% (w/w). The preferred hydrophilic portion in the internal layer of the present invention is pullulan.

The internal layer also contains an equi-mobility salt such as potassium chloride, potassium nitrate, ammonium chloride, lithium acetate, and the like.

Acceptable polymers used in the semipermeable membrane layer include chlorosulfonated polyethylene polymers and cellulose acetate butyrate polymers. The polymer used in the example is chlorosulfonated polyethylene. It is available from Scientific Polymer Products, Ontario, NY, USA.

Figure 7:
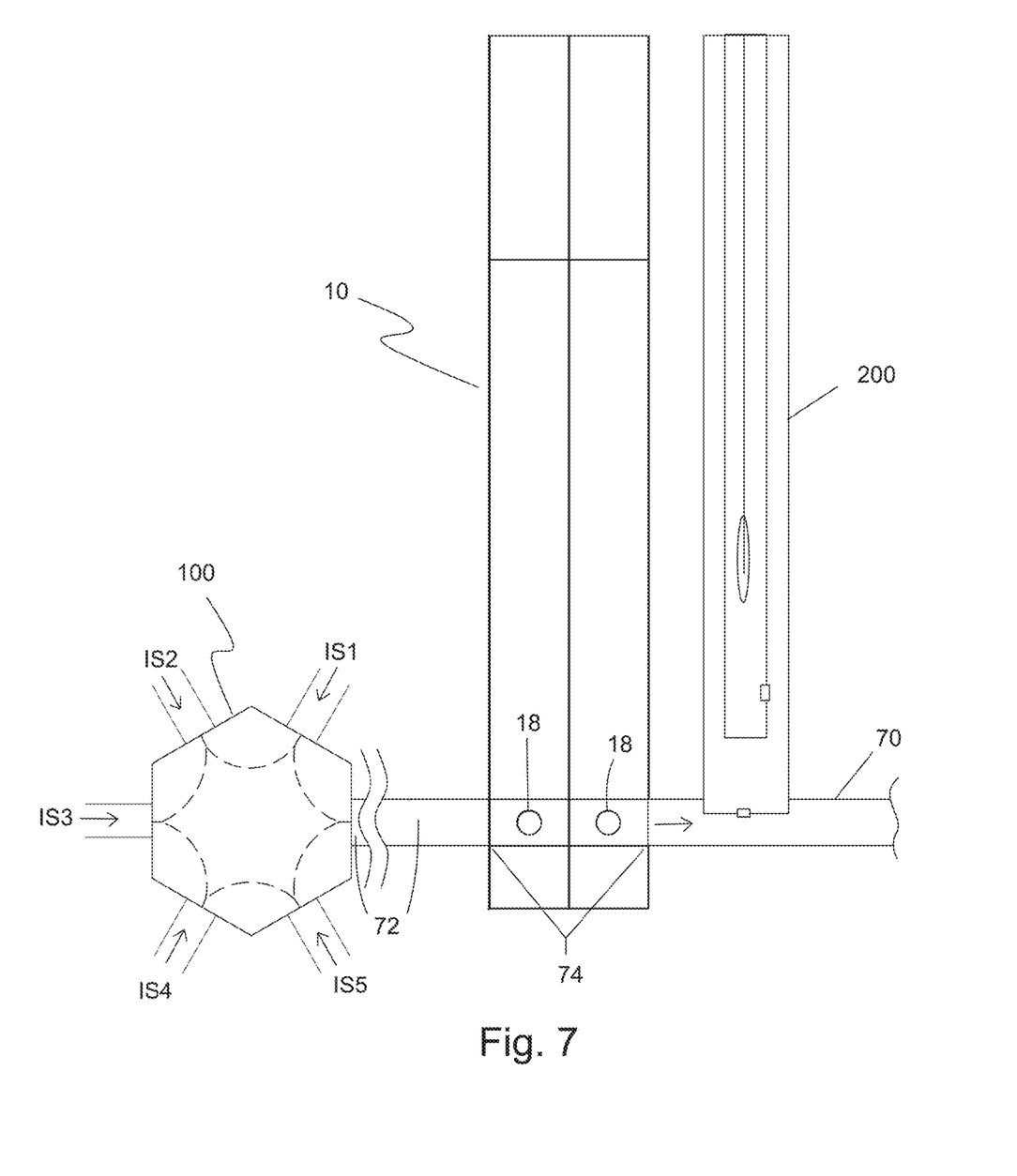
FIG. 7 is an illustrative top view of the potentiometric reference sensor connected to a flow cell for testing the stability and reproducibility of the junction potential of the reference sensor.

FIG. 7 is a top view illustration showing the potentiometric reference sensor 10 connected to a flow cell 70 for determining the junction potential of the reference sensor 10. Flow cell 70 has a test chamber 74 in and one or more reference electrode(s) 18 are disposed. Test chamber 74 has a test chamber inlet 72 connected to a six-way valve 100 to provide five test samples each having a different ionic strength. A predefined amount of each of the five test samples is supplied to test chamber 74 in series for a determining the junction potential of the reference sensor(s) 10 in each of the five test samples. It is understood that the reference sensor 10 is electrically connected to a standard double junction reference electrode 200 and both are connected to proper electronics to perform the junction potential measurement.

Preparation of the Internal and Semipermeable Membrane Layer Compositions

The reagent layer composition for the hydrophilic mixture used to create the internal layer is preferably prepared in two steps, although it may be prepared in one step:

Step 1: Adding together 750 mg of Pullulan (amorphous polysaccharide) and 3 ml of 3 mol/L KCl solution.

Step 2: Mixing the components in Step 1 above until the amorphous polysaccharide is completely dissolved in the KCl solution.

The reagent layer composition for the cover membrane solution used to create the semipermeable membrane is also preferably prepared in two steps although it too may be prepared in one step:

Step 1: Adding 8-10 wt % of one of chlorosulfonated polyethylene polymer or cellulose acetate butyrate in THF/Cyclohexanone.

Step 2: Mixing the ingredients in Step 1 together forming the cover membrane solution.

Sensor Construction

Assembly of the various embodiments of the present invention is relatively straightforward. Generally, the insulating base layer 20 and insulating and reagent holding layer 30 are laminated to each other followed by dispensing the appropriate reagent mixture into the reagent holding opening.

Figure 2:
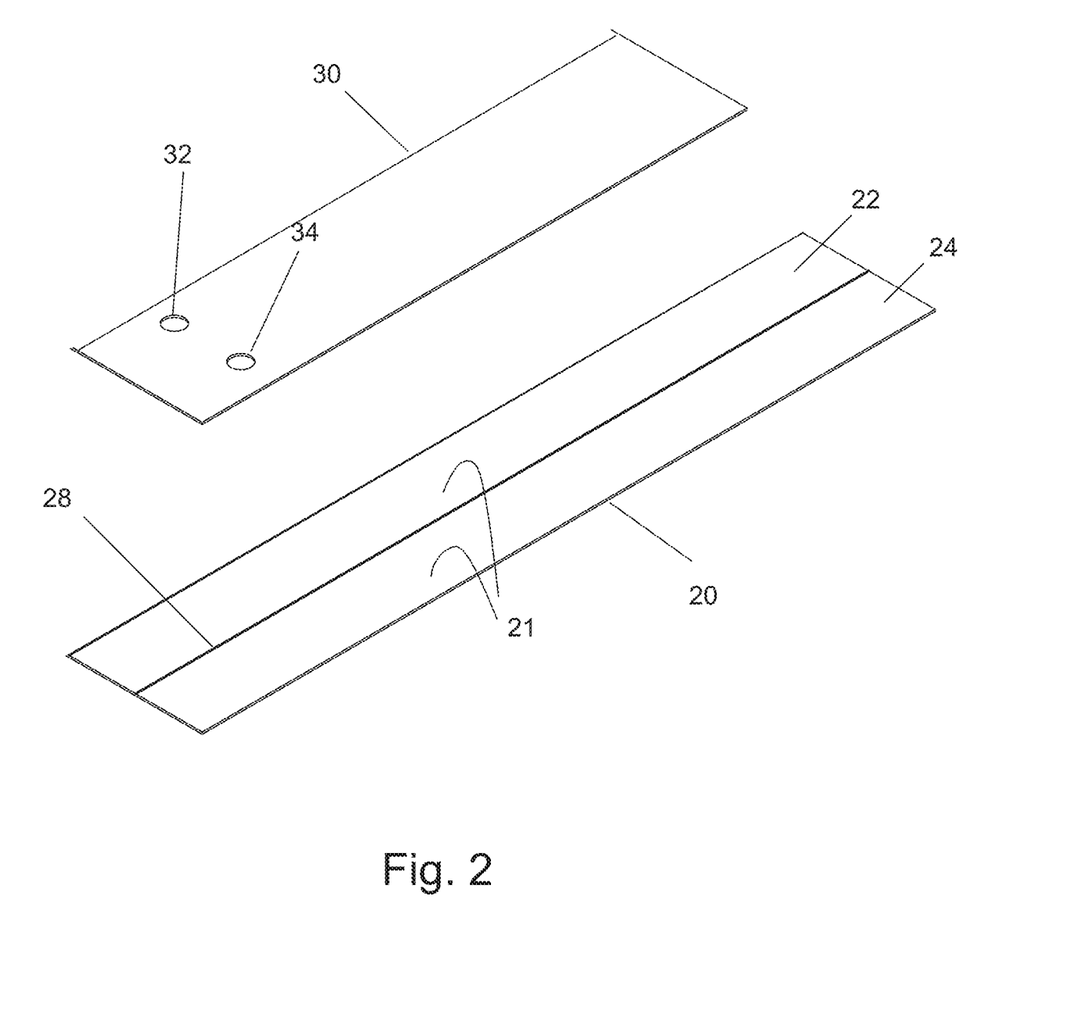
FIG. 2 is an exploded view of the embodiment in FIG. 1 showing the two component layers of the potentiometric reference sensor.

More particularly for the 2-layer configuration shown in FIG. 1, a piece of a palladium-coated, polyester film (coated on only one side) is cut to shape as illustrated in FIG. 2 forming base layer 20 of sensor 10. Even though mechanical scribing is an option, a laser is preferably used to score the conductive palladium polyester film. As illustrated in FIG. 2, the film is scored by the laser such that at least two electrode areas at sample fluid end 14 and at least two contact points 22 and 24 are formed at electrical contact end 16. If only the potentiometric reference sensor 10 is being made, then only one electrode area at sample fluid end 14 and one contact point at electrical contact end 16 are formed. The scoring line is very thin but sufficient to create two separate and distinct electrically conductive paths. If only the potentiometric reference sensor 10 is being made, an optional scoring line may be made along the periphery of the reference sensor 10 to reduce the likelihood of static potential effects on the reference sensor 10. A piece of one-sided adhesive tape is then cut to size and shape, forming insulating and electrode delineating layer 30 so that it will cover a major portion of conductive layer 21 of base layer 20 except for exposing a small electrical contact area illustrated in FIG. 1 by reference number 16.

Before attaching insulating and electrode delineating layer 30 to base layer 20 in the combination sensor, at least two openings 32 and 34 of substantially equal size are punched by laser, or by mechanical means such as a die-punch assembly, creating electrode openings 32 and 34 in insulating and electrode delineating layer 30. The shape of the electrode openings may be any shape. In the illustrated embodiment, the openings are circular. The preferred hole size for openings 32 and 34 has a typical diameter of about 0.030 in. (0.76 mm) but may be any size. As illustrated in FIG. 2, electrode openings 32 and 34 are aligned with each other and have a spacing of about 0.020 in. (0.508 mm) to about 0.050 in. (1.27 mm) between adjacent openings. The circular openings are for illustrative purposes only. It should be understood that the shape and size of the openings or the distance between them is not critical. The circular openings do not have to be substantially equal in size so long as the ratio of the surface areas remains substantially constant. Although the arrangement of the electrodes may be any combination, the preferred arrangement of the electrodes formed in openings 32 and 34 is W (working electrode) and R (potentiometric reference electrode) as positioned from the test chamber inlet 72. Insulating and electrode delineating layer 30 is then attached to base layer 20 in such a way as to define the electrode wells for creating working electrode W and reference electrode R. It is contemplated that if only the reference sensor 10 is being made, the position of reference sensor 10 in the sample chamber 70 would be placed in a similar positional arrangement as previously described.

To create the potentiometric reference sensor, a predefined amount of hydrophilic mixture is dispensed into the potentiometric reference electrode well 34 to completely cover the Ag/AgCl electrode and dried. For example, it may be air dried for few minutes at room temperature or dried for a lesser time at 37° C. forming the internal layer. Drying for a shorter time period at a temperature above room temperature allows for a more efficient manufacturing process. The internal layer mixture and its composition is as described above. During this drying process, the amorphous polysaccharide(s) and the potassium chloride deposit onto the metal layer as the water from the 3 mol/L KCl solution evaporates. The amorphous properties of the polysaccharide(s) are such that the polysaccharide(s) can be mixed with a high concentration of salt (i.e. over saturation) without any separation of the polysaccharide(s) and the salt as the polysaccharide(s)/salt solution dries into a homogeneous, internal layer film. This formed internal layer accelerates salt dissolution when in contact with water vapor that diffuses across the cover membrane, which generates ions quickly and begins to compensate junction potential at the interface of semipermeable membrane while stabilizing the Ag/AgCl potential on a planar array.

Next, the cover membrane solution is dispensed onto the internal layer so that the solution completely covers the internal layer. The cover membrane solution is either air dried overnight at room temperature or dried for 30 seconds or more at 37° C. During this process, the cover membrane component (i.e. the chlorosulfonated polyethylene) forms a hydrophobic layer that is permeable to water vapor and ions. In the case of this potentiometric reference sensor, water vapor diffuses from a sample solution in which the potentiometric reference sensor is exposed into the internal layer dissolving the salt whereby the cations and anions from the equi-mobility salt transport through the semi-permeable membrane layer to the sample solution thereby preventing fluctuation in a junction potential at the sample/cover membrane interface when the internal layer is hydrated by either a calibrant or sample. As discussed previously, the semipermeable membrane layer allows diffusion of water vapor and ions across the cover membrane while the internal layer contains water soluble hydrophilic polymers and salt, which makes electrical connections between the working electrode and the reference electrode in a sensor array when measuring specific species in a sample or, in the case of determining the stability of the potentiometric reference sensor junction potential, makes electrical connections to a standard double junction reference electrode shown in FIG. 7.

The length of time required to dry the reagents is dependent on the temperature at which the drying process is performed.

Testing the Stability of the Potentiometric Reference Sensor's Junction Potential One or more potentiometric reference sensor(s) 10 were connected to a flow cell as illustrated in FIG. 7 along with a standard double junction reference electrode 200. When a fluid sample is supplied to a potentiometric reference sensor of the present invention shown in FIG. 1, the fluid sample enters the flow cell 70 and flows over electrodes W and R, and across the double junction reference electrode 200 and is stopped for a predefined period of time.

Potentiometry was used to measure the junction potential of reference sensor 10 using a potentiostat such as Lawson Labs EMF16 potentiostat, Malvern, PA The potentiometric reference sensor made like those shown in FIG. 1 and described above were used to test the junction potential of the reference sensor 10 of the present invention when exposed to various ionic strength solutions (80-200 mmol/L) after an initial 80 seconds of hydration in one of the ionic strength solutions.

Example 1

Demonstration of the Stability and Reproducibility of the Potentiometric Reference Electrode Junction Potential at Different Levels of Ionic Strength Solutions Liquid samples with different ionic strengths (IS1 to IS5) were used to determine the stability of the junction potentials of the single-use, disposable, reference sensor of the present invention. The junction potentials were measured using the potentiometric reference sensor of the present invention against a standard double junction reference electrode. A potentiostat was used to measure the junction potential between the disposable, single-use, reference sensor 10 of the present invention and the standard double-junction reference electrode 200. The potentiostat was a Lawson Labs EMF16 potentiostat, Malvern, PA The procedure involved an initial solution having ionic strength of 140 mmol/L being flowed into the flow cell to each reference sensor being tested as well as the double-junction reference electrode and stopped, allowing the sample solution to stay in the flow cell for 80 seconds to hydrate the internal layer of the potentiometric reference sensor. At the end of the 80-second hydration period, the junction potential is measured. Following the initial ionic strength sample, four additional, consecutive samples are each flowed into the flow cell at approximately forty (40) second intervals, stopped and the potential measured. At approximately each 40 second interval, the junction potential is measured as shown in Table 1 below.

In this example, multiple potentiometric reference sensors using the palladium substrate were made for testing the junction potential of the reference sensor. The results are shown in Table 1.

TABLE 1

| Time | Junction Potential (mV) | | | | | Ionic Strength Solution |
|---|---|---|---|---|---|---|
| (seconds) | Sensor R1 | Sensor R2 | Sensor R3 | Sensor R4 | Sensor R5 | (mmol/L) |
| 79 | −5.67 | −5.99 | −5.35 | −5.75 | −5.39 | 140 |
| 120 | −5.61 | −6.01 | −5.42 | −5.89 | −5.46 | 80 |
| 165 | −5.68 | −6.00 | −5.39 | −5.85 | −5.35 | 100 |
| 202 | −5.64 | −5.93 | −5.34 | −5.82 | −5.38 | 160 |
| 240 | −5.69 | −6.01 | −5.33 | −5.82 | −5.41 | 200 |
| Average | −5.66 | −5.99 | −5.36 | −5.83 | −5.40 | |
| SD | 0.03 | 0.04 | 0.04 | 0.05 | 0.04 | |

Each ionic strength solution was tested using 5 disposable potentiometric reference sensors 10 for the duration of time from about 80 seconds to about 240 seconds. The average value was calculated and is displayed in Table 1. The standard deviation value for each reference sensor tested is also provided.

Figure 8:
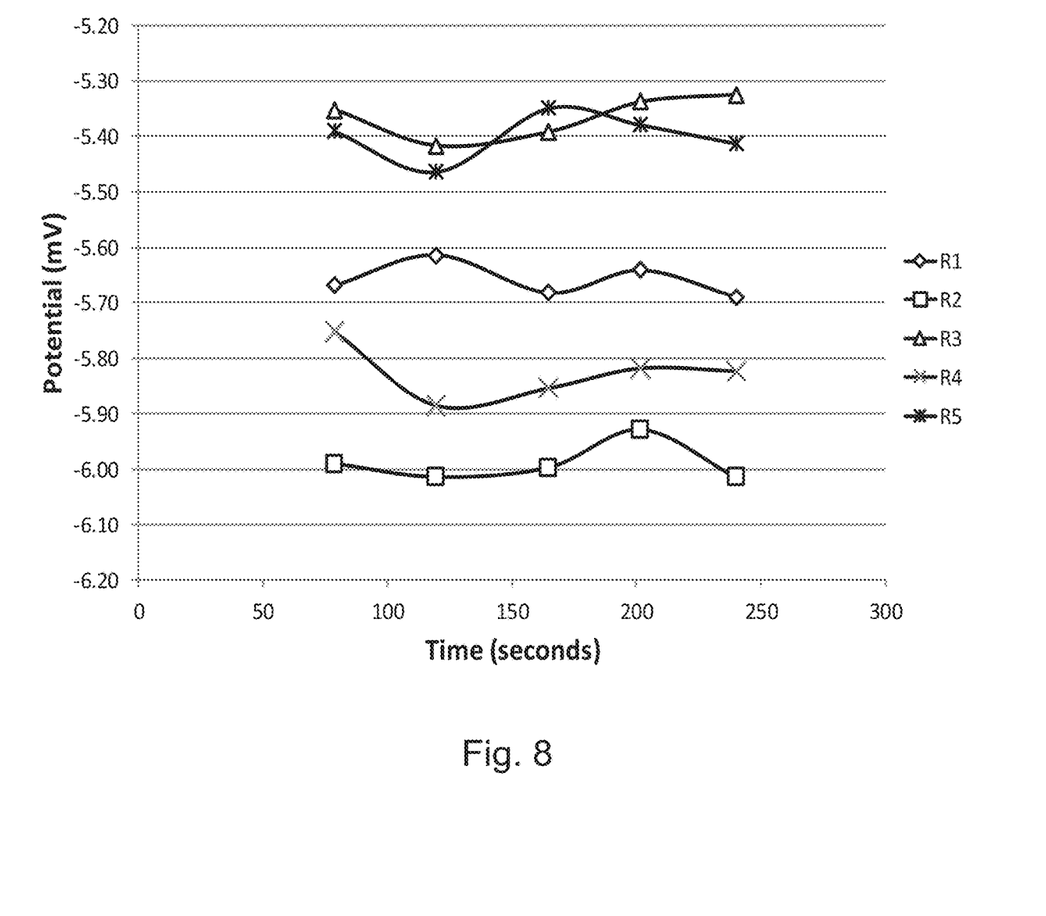
FIG. 8 is a graphic illustration showing the stability of the potentiometric reference sensor junction potential readings of the present invention relative to a double-junction reference electrode in various ionic strength solutions.

FIG. 8 shows the junction potential response of the potentiometric reference electrode/sensor of the present invention (i.e. the internal layer/semi-permeable cover membrane layer electrode) to varying ionic strength aqueous solutions of 140 mmol/L (IS1), 80 mmol/L (IS2), 100 mmol/L (IS3), 160 mmol/L (IS4), and 200 mmol/L (IS5). As shown in FIG. 8, the millivolt change in the single-use potentiometric reference sensor does not appear to be related to the ionic strength of the solutions. The measured overall millivolt variations for a particular reference sensor was less than +/−0.1 mV.

The junction potentials are relatively stable and don't appear to fluctuate throughout the measurement of the five ionic strength solution ranges mentioned above. The data indicates that the cover membrane allows hydration of the internal layer relatively quickly, adequate ion releasing rate (which is enough to prevent any aberration in the junction potential of the reference sensor), and maintains high ion concentration for a relatively long term (approximately 4 minutes) when in contact with aqueous solution. The data further indicates that the junction potential of one reference sensor 10 to other similar reference sensors 10 is relatively consistent between reference sensors. The junction potential difference from one reference sensor 10 to another reference sensor 10 for a given ionic strength solution is less than +/−0.33 mV. This indicates that the potentiometric reference electrode 10 of the present invention may be made and used without having significant changes in the junction potential from one reference electrode 10 to another reference electrode 10 making it suitable as a single-use, disposable potentiometric reference sensor.

The advantages of the present invention over prior art single-use potentiometric reference sensors includes zero maintenance, accessibility, ease of use, reduction of contamination, cost effectiveness, quick analysis, convenience, etc.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A single-use disposable potentiometric reference sensor comprising:
   an insulating base substrate;
   an insulating layer disposed over the insulating base substrate, wherein the insulating layer has an opening formed therein which terminates over the insulating base substrate;
   a reference electrode at least partially disposed within the opening of the insulating layer over the insulating base substrate;
   an internal layer disposed on the reference electrode within the opening of the insulating layer, wherein the internal layer is an amorphous salt layer that includes an amorphous polysaccharide and a salt having equimobility cations and anions; and a semipermeable cover membrane disposed on the internal layer within the opening of the insulating layer such that at least a portion of the semipermeable cover membrane physically contacts the internal layer, wherein the semipermeable cover membrane has water vapor permeability and ion permeability.

2. The single-use disposable potentiometric reference sensor of claim 1 wherein:
the amorphous polysaccharide comprises at least one of pullulan, dextran, and amylose;
the salt comprises at least one of potassium chloride, potassium nitrate, ammonium chloride, and lithium acetate;
the semipermeable cover membrane comprises at least one of a chlorosulfonated polyethylene polymer and a cellulose acetate butyrate polymer;
the amorphous polysaccharide has amorphous properties such that when over saturated with the salt, the amorphous polysaccharide and the salt do not separate when the internal layer is formed; and
the internal layer includes a matrix of the amorphous polysaccharide and the salt having equi-mobility cations and anions.

3. The single-use disposable potentiometric reference sensor of claim 1, further comprising an electrically conductive layer disposed on the insulating base substrate, wherein the electrically conductive layer is sandwiched between the insulating layer and the insulating base substrate such that the opening reaches the electrically conductive layer but does not reach the insulating base substrate.

4. The single-use disposable potentiometric reference sensor of claim 3, wherein the reference electrode is disposed on the electrically conductive layer within the opening of the insulating layer.

5. The single-use disposable potentiometric reference sensor of claim 1 wherein the internal layer is disposed on the reference electrode within the opening of the insulating layer such that at least a portion of the internal layer physically contacts the reference electrode.

6. The single-use disposable potentiometric reference sensor of claim 5 wherein:
substantially all of a lower surface of the internal layer physically contacts the reference electrode; and
substantially all of an upper surface of the internal layer physically contacts the semipermeable cover membrane.

7. The single-use disposable potentiometric reference sensor of claim 1 wherein:
the internal layer is disposed directly on the reference electrode such that the internal layer completely covers the reference electrode within confines of the opening formed in the insulating layer; and
the semipermeable cover member is disposed directly on the internal layer such that the semipermeable cover member completely covers the internal layer within confines of the opening formed in the insulating layer.

8. The single-use disposable potentiometric reference sensor of claim 1 wherein:
the internal layer is a hydrophilic, water-soluble polymer layer which includes the amorphous salt layer and is capable of stabilizing all other chemicals in the internal layer and the semipermeable cover membrane to the reference electrode; and
the semipermeable cover membrane is a hydrophobic polymer layer.

9. The single-use disposable potentiometric reference sensor of claim 1 wherein the reference sensor is configured such that a fluid sample interacting with the reference sensor has access to react with the internal layer only through the semipermeable cover membrane.

10. The single-use disposable potentiometric reference sensor of claim 1 wherein the reference electrode, the internal layer, and the semipermeable cover membrane are provided in a stacked arrangement such that a fluid sample is able to contact the semipermeable cover membrane only from a first side of the semipermeable cover membrane which opposes a second side of the semipermeable cover membrane that physically interfaces directly with the internal layer.

11. The single-use disposable potentiometric reference sensor of claim 1 wherein the reference electrode, the internal layer, and the semipermeable cover membrane together constitute a three-layer structure situated within confines of the opening formed in the insulating layer.

12. The single-use disposable potentiometric reference sensor of claim 1 wherein only the reference electrode, the internal layer, and the semipermeable cover membrane occupy the opening formed in the insulating layer.

13. A multi-layer reagent matrix for making a potentiometric reference electrode into a reference sensor, the reagent matrix comprising:
an internal layer formed from an amorphous salt layer mixture containing an amorphous polysaccharide and a salt, the internal layer overlaying the potentiometric reference electrode, wherein the amorphous polysaccharide has amorphous properties such that when over saturated with the salt, the amorphous polysaccharide and the salt do not separate when the internal layer is formed, wherein the internal layer is a mixture of potassium chloride and at least one of pullulan, dextran, and amylose, wherein the amorphous polysaccharide is in a concentration range of about 0.02% w/w to about 7.0% w/w in the internal layer; and
a semipermeable cover membrane formed from a cover membrane solution disposed on the internal layer such that at least a portion of the semipermeable cover membrane physically contacts the internal layer, the cover membrane solution containing a hydrophobic polymer, wherein the hydrophobic polymer is water vapor and ion permeable.

14. The reagent matrix of claim 13, wherein:
the semipermeable cover membrane comprises at least one of a chlorosulfonated polyethylene polymer and a cellulose acetate butyrate polymer; and
the internal layer formed from the amorphous salt layer mixture contains a matrix of the amorphous polysaccharide and the salt.

15. A method of forming a single-use disposable electrochemical potentiometric reference sensor, the method comprising:
providing a sensor body having:
an insulating base substrate with at least one conductive path;
an insulating and reagent holding layer disposed over the insulating base substrate, wherein the insulating and reagent holding layer has at least one reagent holding opening formed therein, which terminates over the insulating base substrate and exposes a portion of the at least one conductive path; and
a reference electrode at least partially disposed within the at least one reagent holding opening over the insulating base substrate;
disposing an amorphous salt layer mixture containing an amorphous polysaccharide and a salt having equimobility cations and anions into one of the at least one reagent holding opening on the reference electrode, wherein the amorphous polysaccharide is selected from the group consisting of pullulan, dextran, and amylose;

drying the amorphous salt layer mixture forming an internal layer that is an amorphous structure layer;

disposing a cover membrane solution containing a hydrophobic polymer onto the internal layer; and drying the cover membrane solution forming a semipermeable cover membrane such that at least a portion of the semipermeable cover membrane physically contacts the internal layer, wherein the semipermeable cover membrane has water vapor permeability and ion permeability.

16. The method of claim 15 further comprising forming the amorphous salt layer mixture comprising:

adding together a plurality of components comprising a predefined amount of the amorphous polysaccharide and a predefined amount of 3M salt solution; and mixing the plurality of components forming the amorphous salt layer mixture.

17. The method of claim 15 further comprising:

measuring 750 milligrams of the amorphous polysaccharide; and measuring a volume of 3 milliliters of the 3M salt solution.

18. The method of claim 15 further comprising forming the cover membrane solution comprising:

measuring a predefined amount of the hydrophobic polymer that is one of chlorosulfonated polyethylene polymer or a cellulose acetate butyrate polymer; and mixing the hydrophobic polymer in a predefined amount of THF/cyclohexanone forming the cover membrane solution.

* * * * *